United States Patent
Chamanzar et al.

(10) Patent No.: US 10,857,394 B2
(45) Date of Patent: Dec. 8, 2020

(54) RECONFIGURABLE ULTRASONICALLY SCULPTED OPTICAL BEAM PATHS

(71) Applicant: Carnegie Mellon University, Pittsburgh, PA (US)

(72) Inventors: Maysamreza Chamanzar, Pittsburgh, PA (US); Yasin Karimi, Pittsburgh, PA (US); Matteo Giuseppe Scopelliti, Pittsburgh, PA (US)

(73) Assignee: CARNEGIE MELLON UNIVERSITY, Pittsburgh, PA (US)

(*) Notice: Subject to any disclaimer, the term of this patent is extended or adjusted under 35 U.S.C. 154(b) by 0 days.

(21) Appl. No.: 16/522,230

(22) Filed: Jul. 25, 2019

(65) Prior Publication Data
US 2020/0033648 A1   Jan. 30, 2020

Related U.S. Application Data

(60) Provisional application No. 62/764,295, filed on Jul. 26, 2018.

(51) Int. Cl.
- *A61N 7/00* (2006.01)
- *A61B 5/00* (2006.01)
- *G02F 1/125* (2006.01)

(52) U.S. Cl.
CPC .............. *A61N 7/00* (2013.01); *A61B 5/0077* (2013.01); *G02F 1/125* (2013.01); *A61N 2007/006* (2013.01); *A61N 2007/0073* (2013.01)

(58) Field of Classification Search
None
See application file for complete search history.

(56) References Cited

U.S. PATENT DOCUMENTS

| | | | | |
|---|---|---|---|---|
| 6,738,653 | B1* | 5/2004 | Sfez | A61B 5/14553 600/309 |
| 7,898,649 | B2* | 3/2011 | Masumura | A61B 5/4312 356/73 |
| 8,280,494 | B2* | 10/2012 | Masumura | A61B 5/0059 600/437 |
| 10,299,682 | B1* | 5/2019 | Yang | G01B 9/0201 |
| 10,499,815 | B2* | 12/2019 | Nishihara | A61B 5/708 |
| 2005/0107694 | A1* | 5/2005 | Jansen | B82Y 10/00 600/431 |
| 2009/0069674 | A1* | 3/2009 | Masumura | A61B 5/0073 600/425 |
| 2009/0069676 | A1* | 3/2009 | Nishihara | A61B 5/0097 600/437 |
| 2011/0142316 | A1* | 6/2011 | Wang | G06T 11/006 382/131 |
| 2016/0066792 | A1* | 3/2016 | Oyama | A61B 5/4312 600/407 |
| 2020/0033648 | A1* | 1/2020 | Chamanzar | A61N 7/00 |

* cited by examiner

*Primary Examiner* — Rhonda S Peace (57) ABSTRACT

Disclosed herein is a novel reconfigurable spatial and temporal light modulation method that exploits the imaging medium itself by employing a multi-element ultrasonic transducer array as an in-situ acoustic modulator. The medium density can be modulated using different ultrasonic pressure patterns to pattern an incident collimated beam of light.

21 Claims, 10 Drawing Sheets
(10 of 10 Drawing Sheet(s) Filed in Color)

RECONFIGURABLE ULTRASONICALLY SCULPTED OPTICAL BEAM PATHS

RELATED APPLICATIONS

This application claims the benefit of U.S. Provisional Patent Application No. 62/764,295, filed Jul. 26, 2018, which is hereby incorporated herein in its entirety.

BACKGROUND

Spatial light modulators (SLMs) have major applications in the optics field, including optical signal processing, material processing, laser displays, optical communication and microscopy. To modulate the light spatially, various modalities have been reported in literature such as optically addressed SLMs, acousto-optic (AO) SLMs, and magneto-optic SLMs. These applications require fast beam shaping to achieve high throughput. To meet this criterion, technologies, often under fast feedback control, such as deformable mirrors (DM) and liquid-crystal-based spatial light modulators (LC-SLM), provide fast and active spatial light patterning. However, limitations in the refresh rates (e.g., about 1 kHz for LC-SLM) and number of pixels in each scanning direction (e.g. fast DMs) make them less interesting.

To address these challenges, acousto-optic SLMs provide faster beam patterning control over relatively larger area. Moreover, the intrinsic nature of the acousto-optic SLMs provides complete throughput of light and continuous spatial patterns which makes the acousto-optic effect one of the most popular methods of spatial modulation of laser light intensity.

Among the above-mentioned applications, however, SLMs are of great importance to the biological tissue imaging field as two- and three-dimensional images of living tissue are widely demanded in life sciences. Also, further developments (in terms of scanning rate, number of pixels and scanning time) would benefit the field of medical imaging, medical surgery, e.g., noninvasive surgery, endoscopy and physical therapy. AO-based light modulators provide a fast scanning rate, high precision, and stability. Additionally, acousto-optic SLMs can provide reconfigurable multi-site illumination, in-tissue applications such as simultaneous photo-manipulation of living samples in a variable and temporally dynamic manner (e.g. uncaging of glutamate to activate dendritic spines and cortical neurons in brain) and the stimulation or inhibition of multiple neurons at once to achieve specific excitatory/inhibitory effects.

Optical scattering, a dominant light-matter interaction within biological tissue, poses a very significant challenge, and causes a decrease in the depth of penetration of light as well as a decrease in the spatial resolution. Conventional optical microscopy is limited to about one mean free path (MFP), where MFP describes the average distance that a photon travels between two consecutive scattering events (on the order of 100 μm, but the exact value varies by tissue type and wavelength of the incident light).

To address this issue, recently, wavefront shaping techniques have been proposed to compensate for the scattering-induced phase scrambling. These techniques are dependent on feedbacks from the scattering media, as guide stars, to calculate the light trajectory transmission matrix after measuring the scattering response of tissue sequentially over time. Unfortunately, accurate focusing can require millions of unique measurements, and the scattering response of in vivo tissue changes on a sub-second timescale.

SUMMARY OF THE INVENTION

A novel approach to imaging through a turbid medium is disclosed herein in which the imaging medium is used to fragment the incident collimated beam of light into multiple beams within the medium. A segmented piezoelectric transducer array comprising multiple transducer elements is used to create ultrasonic patterns which modulate the medium density and, as a result, induce a temporary refractive index profile. The refractive index profile contrast confines light at the locations of the profile extrema. By applying appropriate voltage distribution to the electrodes, higher-order azimuthal modes which focus light on multiple in-plane nodes may be excited. Additionally, the patterns can be reconfigured by compressing and expanding the mode shapes by driving the transducer array at its repetitive well-defined resonant frequencies, which excite its higher-order radial modes. Furthermore, the invention enables the capability of mode shape rotation and selective light coupling to the locations of refractive index profile extrema by using stroboscopic illumination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Creating multiple patterns of pressure interference with a multi-segment ultrasonic transducer array.

Cylindrical transducers have become an appealing option due to in-phase pressure adding at the center, whose peak can potentially be orders of magnitude larger than one produced by a planar phased array. The propagation of acoustic waves in a cylindrical cavity can be described by solving the wave equation using the separation of variables method subjected to the rigid wall boundary condition in the polar coordinate system. The general acoustic cavity pressure can be written as:

$$p_{m,n}(r,\varphi,z)=J_m(k_{r_{m,n}}r) \cdot \Phi_m(\varphi) \cdot e^{ik_z z} \quad (1)$$

where m is the azimuthal mode number.

For each value of m, there will be a sequence of solutions which are characterized as radial modes. The corresponding mode numbers have been denoted by n herein. The pressure variation along the axial direction can be considered negligible because the wave source propagation direction (i.e., the radial direction) is normal to the axial direction. Therefore, a uniform propagation along z-axis ($k_z \ll k_{r_{m,n}}$) is a fair assumption. As a result, the radial wavenumber would be $k_{r_{m,n}}=k_{m,n}=2\pi/\lambda_{m,n}=2\pi f_{m,n}C_S$, where $\lambda_{m,n}$, $f_{m,n}$ and $C_S$ are the wavelength of ultrasound in the medium, the transducer driving frequency, and the speed of sound in the medium (in the case of water, $C_S$=1484 μm/s). Due to the periodicity along the azimuthal direction, $\Phi_m(0)=\Phi_m(2\pi)$, $\Phi_m$ either could be cos(mφ) or sin(mφ) or a combination of both, where even and odd components are proportional to cos(mφ) and sin(mφ) respectively.

Figure 1:
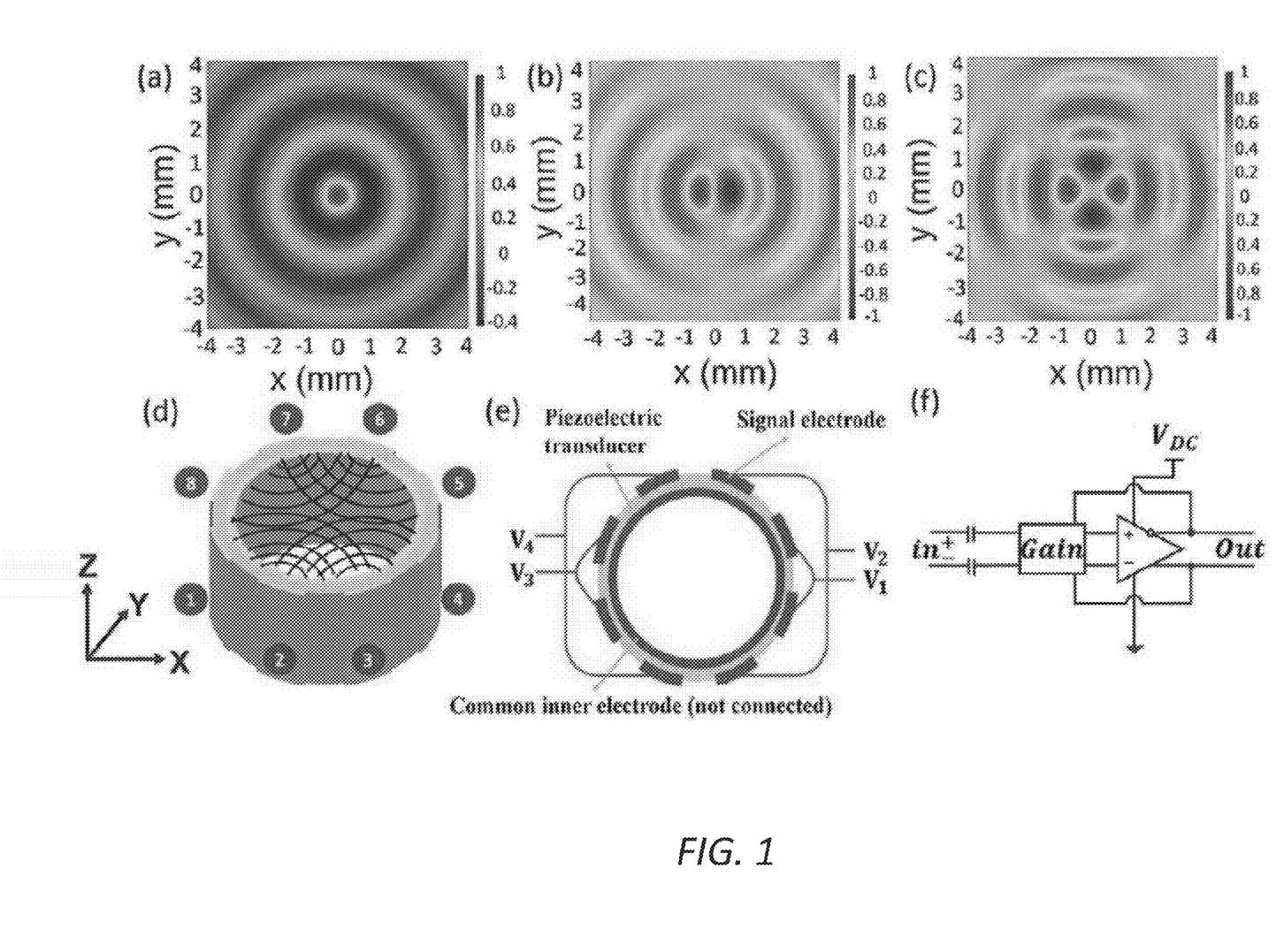
FIG. 1 shows an Eigen-frequency FEM Simulation of the pressure profile in 2D (shown in a window of 8 mm×8 mm) for a fundamental mode (first azimuthal mode, m=0) at 829 kHz, shown in View (a), a dipole mode (second azimuthal mode, m=1) at 848 kHz, shown in View (b) and a quadrupole mode (third azimuthal mode, m=2) at 867 kHz, shown in View (c). View (d) is a schematic of a multi-segment transducer array in a cylindrical geometry. View (e) is a schematic of the voltage distribution. View (f) is a schematic of a differential driving amplifier circuit.

FIG. 1, Views (a-c), show the fundamental mode (m=0, also known as the "breathing" mode), the second mode (m=1, the "dipole" mode), and the third mode (m=2, the "quadrupole" mode), respectively. By following this pattern, the $m^{th}$-order mode will have 2 μm nodes of pressure extrema. The non-uniformity of pressure profile along angular direction to implement benefits the in-plane multi-site illumination.

To excite the desired vibrational modes, the driving voltage signals should be distributed non-uniformly along the circumference of the transducer array. A voltage distribution pattern in the form of $V(\varphi)=V_0 \cos(m\varphi)$ is able to excite the $m^{th}$ azimuthal mode. However, applying a continuous voltage waveform $V(\varphi)$ is difficult. An approximation for such a signal can be achieved by using equally-separated outer electrodes in a vertically-segmented transducer, as shown in View (d) of FIG. 1, with a common inner ground electrode, as shown in View (e) of FIG. 1. At least four segments are required to excite the first three modes. however, to show a proof-of-concept angular rotation of the mode shapes, a multi-modal 8-segment cylindrical transducer array may be used as shown in View (d) of FIG. 1. Due to the even symmetry of the elements, the voltage distribution is presented in the form of a four-element vector. The voltage is set as a sign vector which shows the voltage arrangement, multiplied by a base voltage, keeping the amplitude of the driving signals the same for all elements (V=sign vector ($V_m$)×base voltage (X)). A uniform $V_{J_0}=[V_1, V_2, V_3, V_4]=[1, 1, 1, 1]$ voltage distribution can only excite the fundamental mode (m=0). To primarily excite the dipole mode (m=1), the driving voltages should create two out-of-phase poles. Consequently, the voltage distribution should follow the $V_1=[V_1, V_2, V_3, V_4]=[1, 1, -1, -1]$ pattern. Similarly, for exciting the quadrupole mode (m=2), the voltage distribution should follow the $V_{J_2}=[V_1, V_2, V_3, V_4]=[1, -1, -1, 1]$ pattern that excites primarily the quadrupole mode. It should be realized that an unlimited number of modes can be excited.

Conventional methods to drive Piezoelectric transducers require that independent driving signals are applied to the two terminals of each piezoelectric element. In the described invention herein, an innovative piezo transducer driving method is employed which suggests applying the driving voltage polarization azimuthally. Instead of using two separate channels and applying a 180° phase shift between them, a differential driving technique is used, meaning that the positive pole of the amplifier output is connected to the positive pairs and the negative pole is connected to the negative pairs There are two important advantages in using this method over using two separate driving signals. First, with each leg swinging out of phase with the other, the differential voltage applied to the load is twice that of the output swing of each leg, and, second, measured differentially across the load, the effective slew rate is two times higher than that of a single leg. Based on the two mentioned advantages, the piezo transducer array is driven differentially by the circuit shown in View (f) of FIG. 1. As a result, the inner electrode is floating.

Using Pressure Interference Patterns to Modulate the Refractive Index of the Medium The underlying physics behind the acousto-optic modulator is an acoustic fluctuation generated by a piezoelectric actuator. The piezoelectric transducer launches an ultrasonic wave which is coupled to the target medium. Vibration of the piezoelectric transducer walls generates an ultrasonic interference wave pattern, which causes oscillation in the medium density, and thus in its refractive index. Assuming the transducer walls vibrate co-sinusoidally with the driving frequency ω, the refractive index of the medium can be modeled as:

$$n(r,\varphi,t)=n_o+n_{max}\cdot J_m(k_r,r)\cos(m\varphi)\cdot\sin(\omega t) \quad (2)$$

where $n_0$ is the mean refractive index of the medium, $n_{max}$ is the maximum amplitude of the refractive index variations, and ω is the driving angular frequency.

Figure 2:
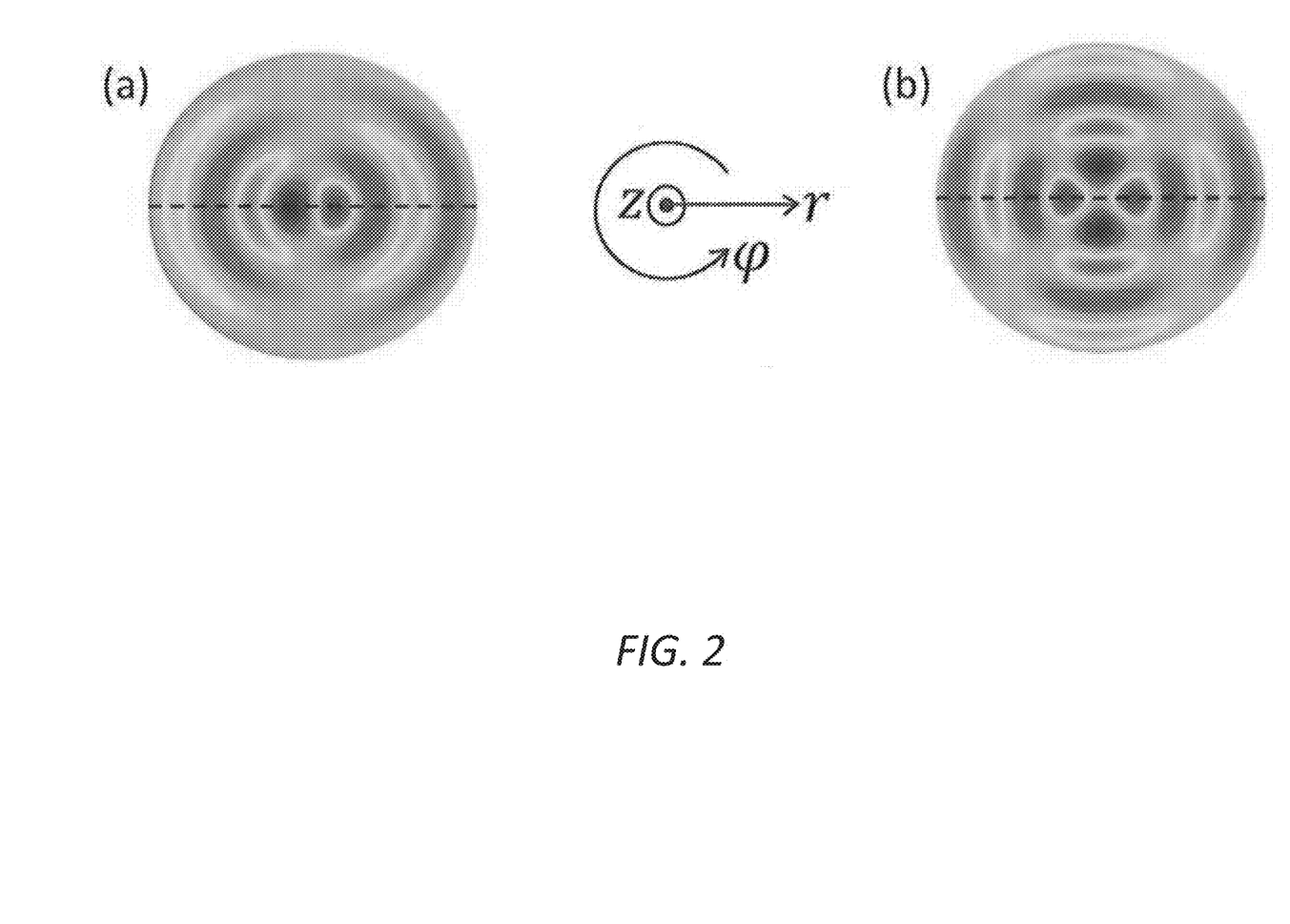
FIG. 2 shows a dipole and quadrupole mode illustrations, in Views (a-b), respectively. View (c) is a pressure profile of the dipole mode at 848 kHz, with the radial distance between the first extrema shown as $r_1$. View (d) is a pressure profile of the quadrupole mode at 867 kHz, with the radial distance between the first extrema shown as $r_2$. View (e) is a refractive index profile corresponding to the pressure profile shown in View (c), View (f) is a refractive index profile corresponding to the pressure profile shown in View (d). View (g) and View (h) are ray tracing simulations showing the axial propagation of the plane wave after passing through a modulated medium, as a function of radial distance from the center of the transducer. It should be noted that the pressure wave is a standing wave, meaning that in a period of the ultrasonic signal, peaks and troughs will alter.

The pressure profiles along the radial direction shown in Views (c-d) of FIG. 2 were obtained using a computer aided simulation, for the dipole and quadrupole modes shown in Views (a-b) of FIG. 2, respectively. Views (e-f) of FIG. 2 show the refractive index profiles corresponding to the pressure profiles.

The refractive index profile was obtained using the pressure profile, due to the fact that the relatively small changes in the medium density (ρ) compared to the static density, enables a linearized version of the Lorentz-Lorenz equation which relates the medium density to the refractive index (n) to be assumed. The same linearized assumption is true between medium density and acoustic standing pressure wave (p) inside the medium. This linearization can be written as:

$$n \propto \rho \propto p \quad (3)$$

As light propagates through the index-modulated medium, it starts deterring toward the locations of the extrema of the refractive index profile. The analogy of the wave-propagation through the medium is similar to that of the graded-index media (e.g. GRIN lens). To simulate the beam formation along the axis of the transducer inside the medium, the ray tracing model in a graded index medium is a fair approximation of the optical beam propagation in such a modulated medium. Ray propagation along a graded index medium is described by the Eikonal equation. This equation is true as long as the paraxial assumption is considered (which is true due to the small variations in the refractive index of the medium, $\Delta n < 5 \times 10^{-4}$). The incident laser light can be approximated as a plane collimated beam of light. As the ray tracing simulations in Views (g-h) of FIG. 2 show, both pressure and refractive index profile extrema magnitudes are the exact values needed to confine light to the center of top surface of the cylindrical array (z=30 mm).

Figure 3:
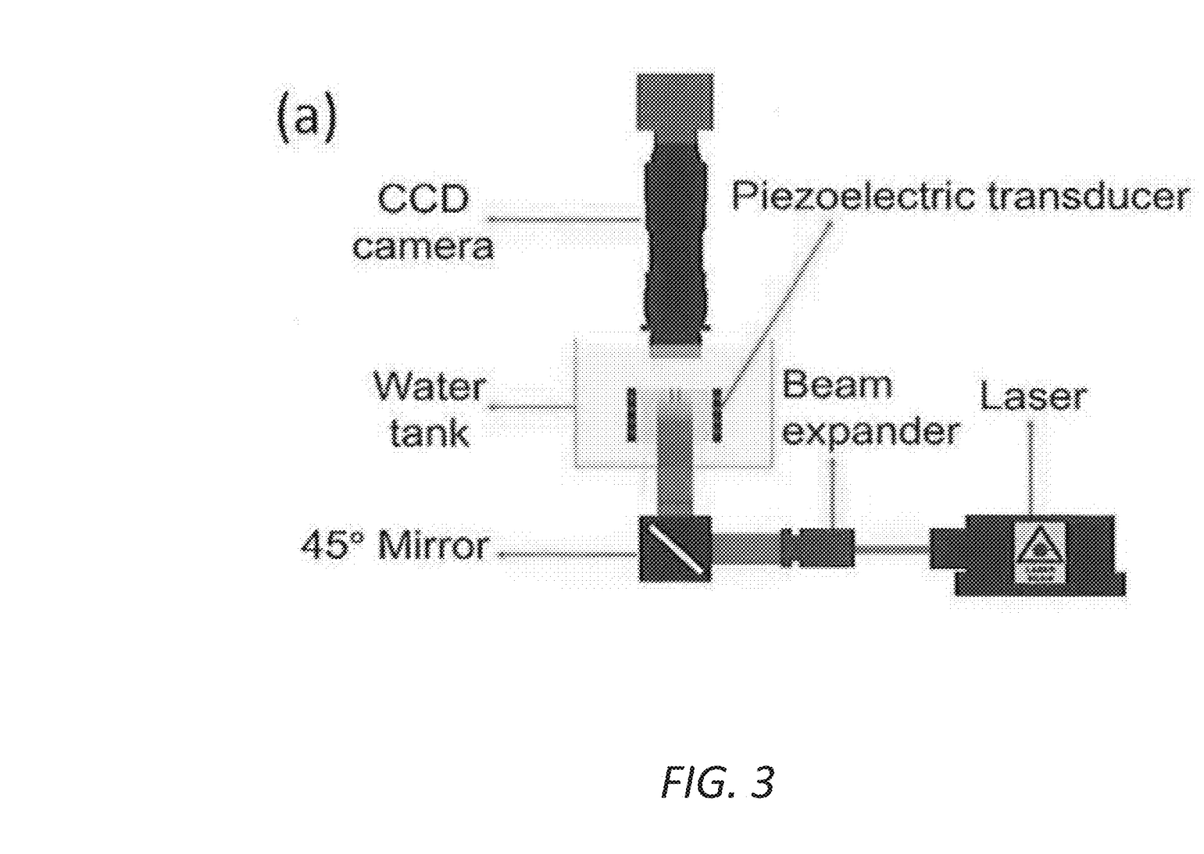
FIG. 3, View (a) is a schematic of an experimental setup. View (b), (top) shows a 1× magnification of the dipole mode at 850 kHz while View (b), (bottom) shows a zoomed-in 6× magnification view of the dipole mode, first lobes and the radial distance between them illustrated as $r_1$. View (c) shows a quadrupole mode at 829 kHz at 1× magnification (top) and zoomed-in at 3× magnification (bottom), showing the first four annular focal points and the distance between them as $r_2$. Views (d-e) show a 3D image reconstruction of the two modes depicted in Views (b-c), respectively, which shows the input incident light is tagged to the location of refractive index extrema after passing through the modulated medium.

To show the experimental realization of the concepts explained so far, a customized setup was designed which schematics is depicted in the View (a) of FIG. 3. An 8-segment piezoelectric transducer (ID=38 mm, OD=44 mm, h=30 mm) was employed. The transducer was totally immersed in deionized water (as the medium). A beam of red light (beam diameter=6 mm, after passing through a beam expander) generated by a laser at the wavelength λ of 650 nm acts as the incident illumination light. A CCD camera was placed focused on the center of top surface of the cylindrical array to image the modulated pattern of light.

Different pressure patterns which were obtained via exciting the first and second acoustic azimuthal modes result in a 3D refractive index modulation of the medium. For instance, to excite the dipole mode at one of the well-defined resonant frequencies at 850 kHz, the voltage distribution was set to be $[V_1, V_2, V_3, V_4]=[23.2$ v, 23.2 v, −23.2 v, −23.2 v]. The formed second azimuthal mode (dipole mode, m=1) is shown in View (b) of FIG. 3.

The third azimuthal mode (quadrupole mode, m=2) is also achievable by changing the voltage distribution to $[V_1, V_2, V_3, V_4]=[19$ v, −19 v, −19 v, −19 v] at 868 kHz as shown in View (c) of FIG. 3.

From Snell's law, the ray path along the axial direction is expected as depicted in Views (g-h) of FIG. 3. Views (d-e) show the experimental results of the dipole and quadrupole modes, respectively. These views were achieved by axial image reconstruction (by moving the camera by a z-axis motor from top surface to the half-height of the transducer). The results compare well with the numerical simulations.

Achieving Spatial Light Modulation by Exciting the Azimuthal and Radial Modes of a Cylindrical Transducer Array As shown above, spatial light modulation is fathomable via driving a multi-segment transducer array at different azimuthal modes by applying an appropriate voltage signal distribution to the transducer array elements. The reconfigurability of the introduced modulator will now be discussed. One of the innovations described herein is controlling all the parameters electronically without physically moving or disturbing the system. The degrees of freedom using which the reconfigurable modulator has been realized in this work are: 1) the driving frequency of the transducer that enables condensation/expansion of the resulting optical mode shapes, 2) rotation of the mode shape which was done by rotating the driving signals applied to the electrodes by one element while preserving the order of the voltage vector, and 3) coupling light to the extrema of the pressure by utilizing a stroboscopic illumination and applying a phase shift between the laser and the transducer driving signals.

Radial Sweeping

Figure 4:
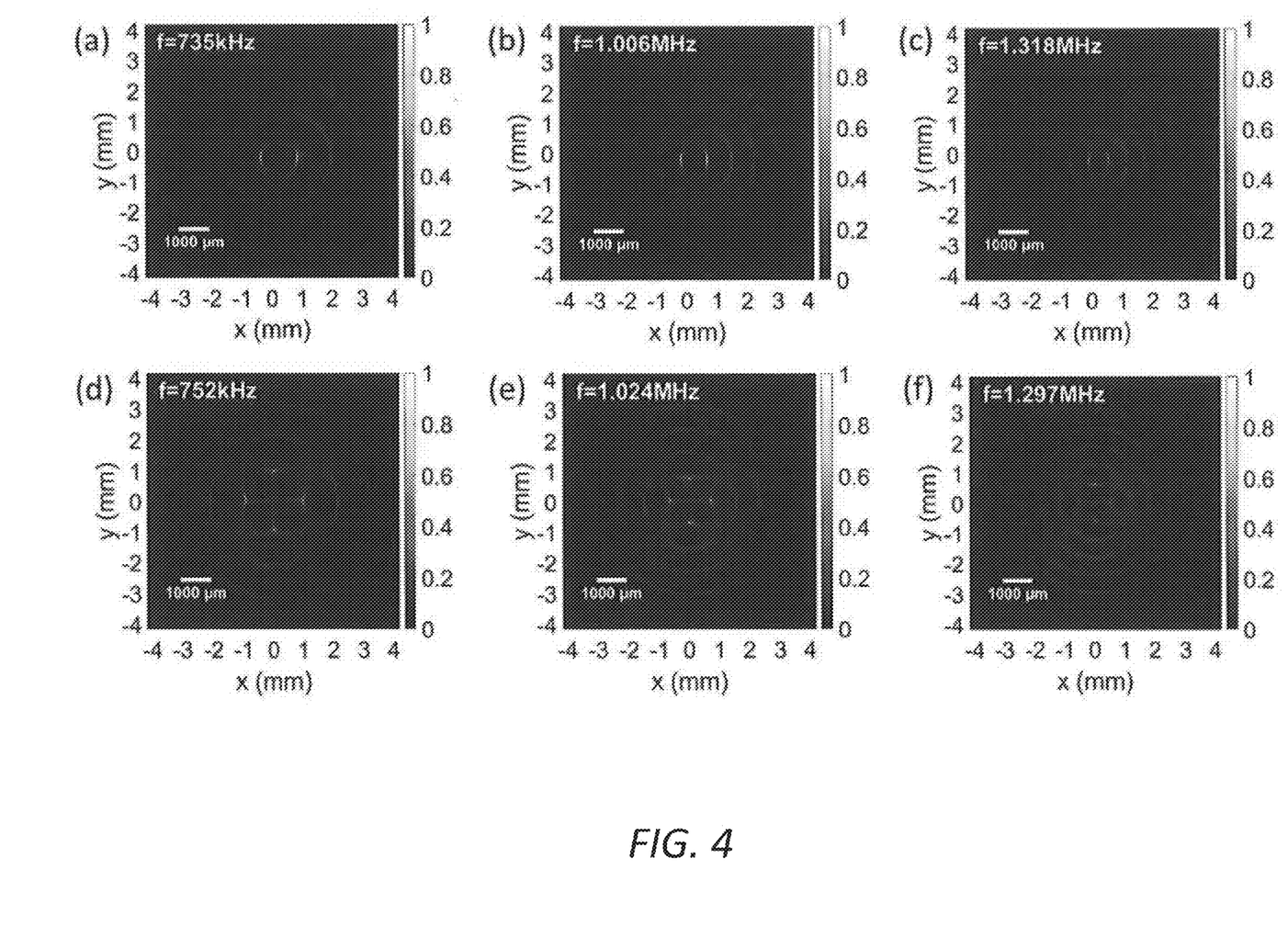
FIG. 4 shows three radial sweeping samples for both dipole and quadrupole modes. The driving frequency is shown in the upper left of the picture for each case. The driving voltage distribution of the dipole and quadrupole modes were set as $[V_1, V_2, V_3, V_4]=[1, 1, -1, -1]X^V$ and $[V_1, V_2, V_3, V_4]=[1, -1, -1, 1] \cdot X^V$ respectively. The base voltage and radial spacing between the focal points are: X=36.5 v, r=1.243 mm in View (a), X=15 v, $r_1$=0.865 mm in View (b), X=60 v, $r_1$=0.657 mm in View (c), X=64 v, $r_2$=1.911 mm in View (d), X=17 v, $r_2$=1.4 mm in View (e) and X=60 v, $r_2$=1.089 mm in View (f).

The dependency of the locations of the pressure profile extrema on the sound wavelength inside the acoustic medium can be well inferred from Eq. (1). The solution of the equation, considering the rigid-wall boundary condition, leads in discrete allowed values of the frequencies that determine the wavenumber for each $k_{r_{m,n}}$. Driving the piezoelectric transducer at these discrete resonant frequencies results in condensation or expansion of the mode shape while preserving the totality of the mode. Views (a-c) of FIG. 4 show three qualitative examples of the dipole mode (m=1) shape compression as the transducer was driven at higher resonant frequencies (thus smaller sound wavelengths). Similarly, Views (d-f) of FIG. 4 show the same behavior while the segmented transducer was driven at different, well-defined resonant frequencies in the quadrupole mode (m=2) shape.

The theory behind the discrete modes supported by a cylindrical cavity are now discussed. The rigid-wall boundary condition dictates $$J'_m\left(\frac{2\pi f r}{C_S}\right) \text{ at } r=a,$$

where a is the inner radius of the transducer, should be zero. This produces the allowed values of frequencies which satisfy the boundary condition that can be expressed as $$f_{mn} = \frac{C_S}{2a}\alpha_{mn},$$

where m is the azimuthal mode number, n is the radial mode number and where $\alpha_{mn}$ is a constant unique to each mode. As a result, the wavenumber would change as the transducer is driven at different radial and azimuthal modes. The spacing between the first extrema around the center of the transducer ($r_1$ and $r_2$, shown in the insets of Views (b-c) of FIG. 3, is determined by the wavenumber, as they occur where the derivative of the Bessel function is equal to zero (See Views (c-d) of FIG. 2). The mode constant can be approximated as $$\alpha_{mn} = n + \frac{m}{2} - \frac{3}{4}; m < n \gg 1.$$

The constant spacing between the consecutive radial modes can be inferred which, in this case, $$\left(a = 19 \text{ mm and } C_S = 1484\frac{m}{s} \text{ in water}\right)$$

would be $$\frac{C_S}{2a} = 39 \text{ kHz}.$$

In the set of experiments shown in Views (a-f) of FIG. 4, the frequency range for the dipole mode start from f=735 kHz, which matches well with the predicted frequency of (m=1, n=19) mode at $f_{1,19}$=732 kHz. This sweeping frequency range ends at f=1.318 MHz, which compares with the frequency of (m=1, n=34) at $f_{1,34}$=1.318 MHz. The same trend is true for the quadrupole mode as well, as the experimental frequency range starts at f=752 kHz, corresponding to a theoretically predicted frequency of $f_{2,19}$=751 kHz, and ends at f 1.297 MHz, corresponding to $f_{2,33}$=1.298 MHz.

Rotation (Angular Sweeping)

Figure 5:
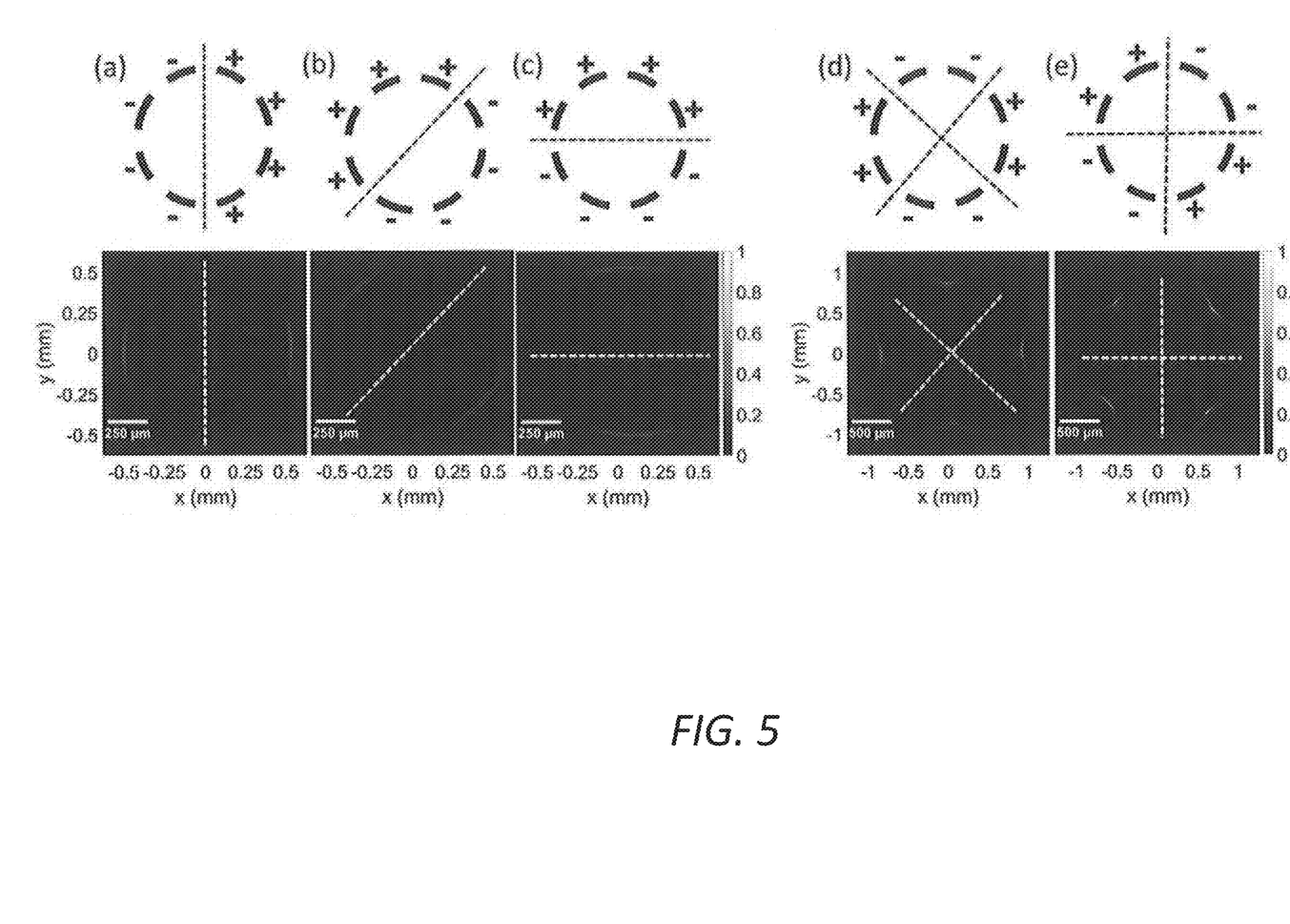
FIG. 5 shows experimental results of the rotation in dipole mode (6× magnification) when the axis was at 0° in View (a), 45° in View (b), 90° in View (c), and the quadrupole mode (3× magnification) at 0° in View (d) and 90° in View (e).

To further expand the spatial modulation domain, a discrete rotation of the mode shapes can be achieved by switching the subsets of driving signals electronically without physically moving the transducer around the circumference. The orientation of the mode shape is determined by that of the driving signals. For example, as it is shown in Views (a-e) of FIG. 5, the mode shape can be rotated around the center of the transducer in a discrete manner. If the two poles of the dipole mode driving signal set are arranged to be segments 3-6 of the multi-segment transducer array in a cylindrical geometry shown in View (d) of FIG. 1, as the positive and the rest as the negative, the mode will be as presented in the View (a) of FIG. 5. Preserving the totality of the two-pole connection configuration and by shifting the elements counterclockwise by one, the mode shape will be rotated by 45°, as shown on View (b) of FIG. 5. Additional one-element shifting will lead into rotation steps of 45°. The same rationale can be applied to the quadrupole mode as depicted in Views (d-e) of FIG. 5. The step size of the rotation is determined by the number of elements. If a cylindrical transducer, that is split into 2M segments, is employed, then the one-element shifting algorithm will produce a rotation by a $$\left(\frac{360}{2M}\right)^\circ$$

step size. By employing an 8-segment transducer, the step size

Selective Light Coupling

Figure 6:
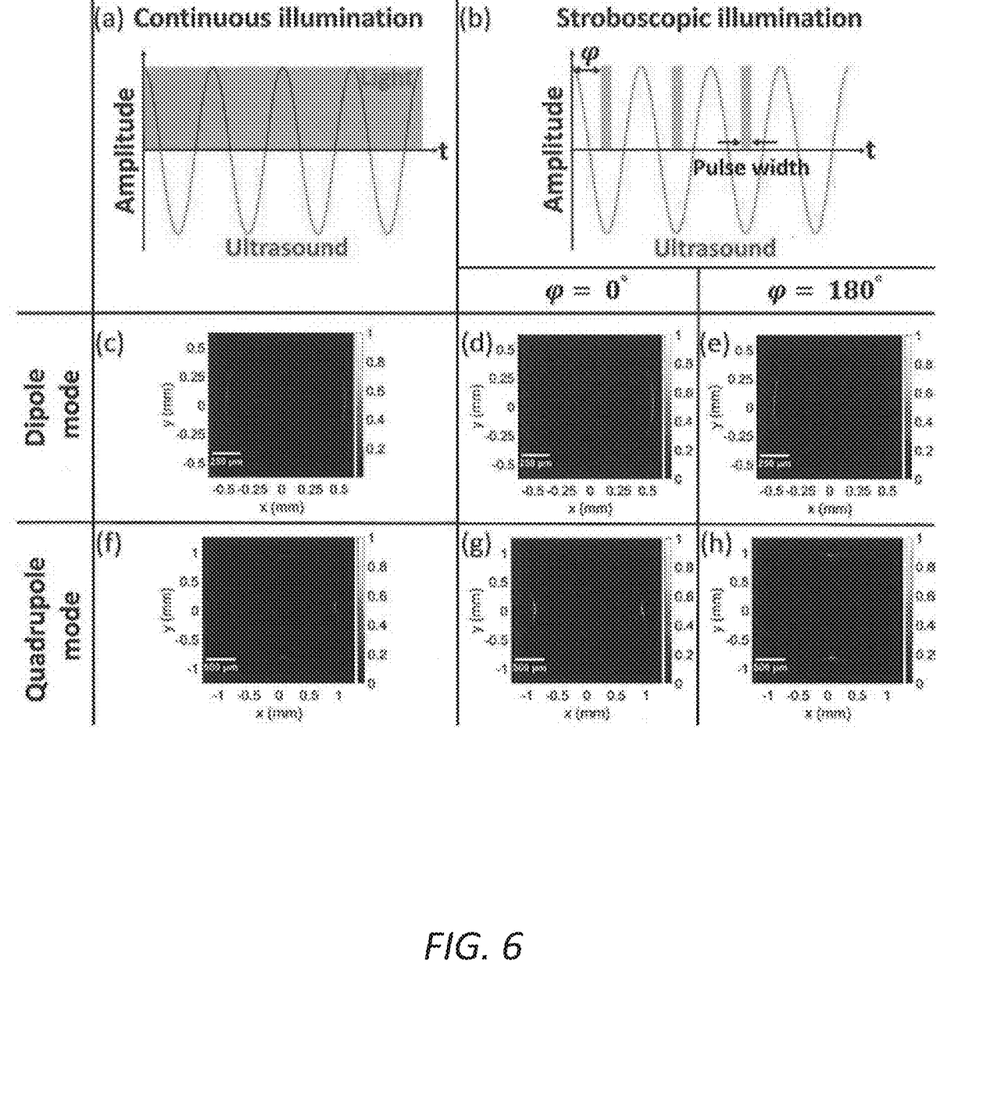
FIG. 6, Views (a) and View (b) Illustrate the continuous and stroboscopic illumination schemes. View (c) shows a dipole mode at 851 kHz and X=17 v by continuous illumination, and by stroboscopic illumination when, in View (d), $\varphi$=0° and in View (e), $\varphi$=180°. View (f) shows quadrupole mode at 830 kHz and X=19 v by continuous illumination and by stroboscopic illumination when, in View (g), $\varphi$=0° and in View (h), $\varphi$=180°.

As discussed so far, the acoustic waves create a standing pressure wave inside the medium and modulate the medium density and thus the refractive index, which is spatially and temporally varying. The pressure nodes will be steady versus time, however, the peaks and troughs of the pressure alter within a period of ultrasound. Consequently, at the locations of the extrema of the pressure profile, a constant rarifying and compressing of medium density thus focusing and dispersing of the light rays occur. Because the operating frequency (on the order of hundreds of kilohertz) of the ultrasound is much higher than the capture rate of the CCD camera, the images captured by camera are effectively "time-average" images. Thus far, all results presented herein have been achieved by using a continuous wave (CW) laser, as shown in View (a) of FIG. 6. The time-average effect can be diminished by reducing the time of illumination. To realize this, a signal generator was used to create pulses which feed the laser. As a result, a stroboscopic illumination, as shown in View (b) of FIG. 6, will be generated. The time span of the laser pulse driving signal (duty cycle of the pulse) over a period of ultrasound signal determine the intensity of modulated light.

A square pulse signal with the duty cycle of 20% was used. Depending on the level of intensity required, the duty cycle can be programmed accordingly. A temporal modulation of the incident light can be also be achieved by aligning the coincidence of illumination and refractive index extrema which can be implemented via applying a proper time delay between the ultrasound and laser driving pulse signal by using a two-channel function generator. Since the extrema of the refractive index profile are out-of-phase at any given time, by setting the phase difference (φ) to be 00 or 180°, the incident light will be tagged to the location of the maxima or minima. The temporal modulation of light is shown in Views (d-e) and (g-h) of FIG. 6 for both m=1 and m=2 azimuthal modes respectively.

A novel method has been described above for modulating an imaging medium to pattern and confine light within the target medium. Furthermore, using the acousto-optic effect, a spatial and temporal patterning of light has been described which employs a multi-segment cylindrical acoustic transducer while being excited at its higher-order modes. All experimental results have been shown using an optically transparent medium (water). In the following section, the feasibility of applying the spatial and temporal light modulation in a scattering medium via modulating the imaging medium density is demonstrated.

Light Interacts with a Medium with Such a Refractive Index Modulation Profile. Optical Beams Will be Sculpted within the Tissue.

As discussed, the conventional methods of imaging widely use an external lens (fixed lens or tunable tag lens) to modulate the wavefront and create a spatial pattern prior to entering the sample to compensate the scattering of the tissue and increase both the depth of penetration and spatial resolution.

A refractive index profile can be embedded within the imaging medium by the ultrasonic interference pressure wave. The formed refractive index profile acts as a "virtual AO-SLM" which creates reconfigurable patterns of light foci. In this way, the embedded refractive index grating will retrieve part of the scattered photons and align them along the shaped changeable trajectories of light. By this means, not only the patterns of in-plane light foci can be reconfigured semi-arbitrarily, but also the embedded index profile helps to increase the penetration of light. As photons travel down into the biological tissue, there is a constant battle between the scattering and confinement. As photons reach to the deeper layers, the number of scattering events increases exponentially and gradually the confinement capability decays. To show this trend of foci contrast degradation, a commonly-used figure of merit called "peak-to-background" ratio (PBR)" is used. This is the ratio between the intensity of the focus and the average intensity of the background surrounding the focus.

The experimental setup is the same as shown in View (a) of FIG. 3, however, water has been replaced as the medium with a scattering solution to mimic the optical properties of biological tissues. Among the most widely used and well-studied tissue phantoms for optical imaging are lipid emulsions similar to milk. A range of different concentrations of 20% Intralipid solutions which represent different levels of scattering have been used. Four different concentrations of Intralipid solutions have been prepared, from 0.52%-(1.3 ml Intralipid diluted with 250 ml water) to 0.64% (1.6 ml Intralipid diluted with 250 ml water) with the step size of 0.04%. The reduced scattering coefficients corresponding to the abovementioned concentrations were measured to be $\mu_{s_1}'=1.489$ cm$^{-1}$, $\mu_{s_2}'=1.578$ cm$^{-1}$, $\mu_{s_3}'=1.667$ cm$^{-1}$ and $\mu_{s_4}'=1.756$ cm$^{-1}$, respectively, by using Oblique Incidence Reflectometry.

These levels of scattering are comparable to some biological thin tissue layers such as Bonghan corpuscles in rats (in vitro measurements) and bovine cornea. The capability of light penetration in biological tissues has been reported as optical thickness (OT[MFP] shows the number of scattering events that ballistic photons experience through the medium; which is commonly defined as OT=$\mu_s$d, where d is thickness of the sample).

Figure 7:
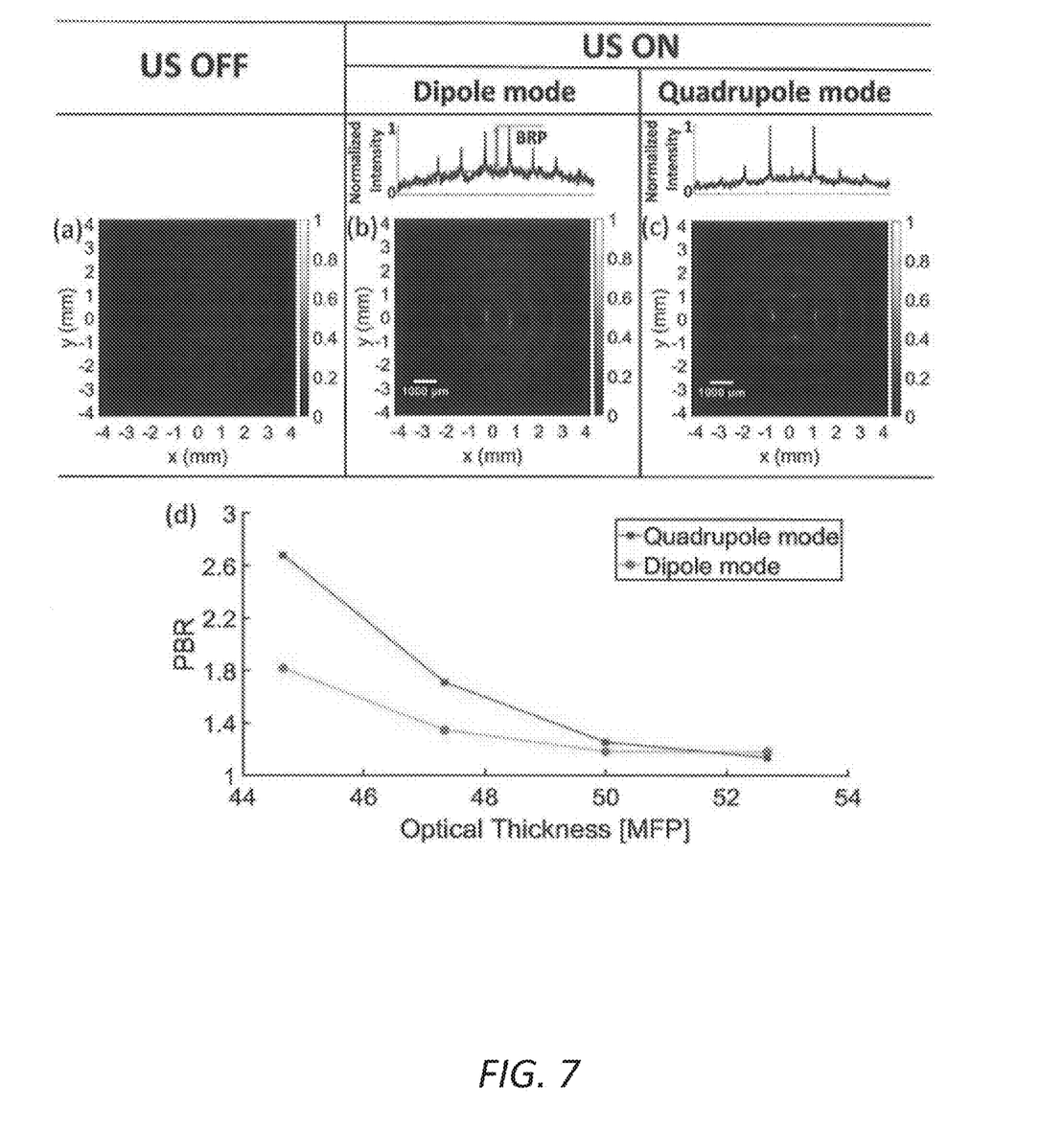
FIG. 7 shows the results of the light modulation. View (a) shows scattered light after passing through while the ultrasound was off. View (b) shows the dipole mode at 853 kHz. View (c) shows the quadrupole mode at 833 kHz. View (d) is a graph showing the peak-to-background ratio vs. different levels of scattering.

The optical thicknesses corresponding to the aforementioned reduced scattering coefficients, considering d=L=30 mm length of the transducer, are 44.67 MFP, 47.34 MFP, 50 MFP, and 52.67 MFP, respectively. These levels of scattering events compare well with that of the light propagating through 1 mm of mouse brain. The camera was focused on the center of top surface of the cylindrical array. View (a) of FIG. 7 shows the dispersion of the input incident light when the ultrasound is off (in the case of OT=47.34 MFP). Views (b-c) of FIG. 7 show the dipole and quadrupole mode shapes which were created by modulating the density of the turbid medium. As indicated in View (d) of FIG. 7, by increasing the number of scattering events, an exponential decay behavior in focusing ability of the SLM is obvious; which shows degradation in the quality of light patterning.

Peak-to-background ratios of >10% could be observed in solutions whose optical thickness were <50 MFP. A frequency shift of −2 kHz has been detected for both azimuthal modes compared to water as the host medium. The shift can be attributed to the change in medium density thus the surrounding mechanical damping on the transducer.

The feasibility of directly using the scattering and inhomogeneous imaging medium itself by
modulating its refractive index and virtually inducing a SLM within the medium is suggested, which can be useful while working in low-scattering tissue layers since the higher level of scattering makes the incident light dispersed regardless of the induced modulation. However, this method can be combined as an add-on for an external acousto-optic SLM which can make a series system and help overcoming the scatteredness of biological turbid tissues. In this range of frequency (700 kHz-1.3 MHz), the loss introduced by the biological tissue to the ultrasound is low (~0.3-0.6 dB/ (cm·MHz), which ensures that the induced ultrasonic pattern will travel through the medium with minimum perturbation and damping.

An acousto-optic spatial and temporal light modulator has been disclosed, not as an external optical device but as a host in-situ medium density modulator. The light patterning may be configured by exciting various azimuthal and radial modes. Additionally, the pattern may be tuned both in the spatial and temporal domain. Spatiotemporal light modulation may be accomplished by exciting higher order azimuthal modes. The spatial tunability may be accomplished by hopping between consecutive radial modes. In that sense, in the case of dipole and quadrupole modes, the mode shape could be expanded/compressed over a radial distance range of $r_1 \subseteq [1.243$ mm-0.657 mm] and $r_2 \subseteq [1.921$ mm-1.089 mm], respectively, which is directly forced by the inner radius of the cylindrical transducer array. The other degree of freedom rotates the mode shape electronically by rotating the voltage signal vector around the transducer by one element, which corresponds to 450, which can be determined by the number of elements employed. Regarding temporal tunability, stroboscopic illumination may be used by which coupling to half of the illuminated nodes at a time is possible.

We claim:

1. A method for inducing a light waveguide in a medium comprising:
   directing ultrasound produced by a transducer array comprising one or more transducer elements into the medium to create a refractive index profile comprising a spatial pattern of refractive indices in the medium;
   wherein the spatial pattern of refractive indices comprises two or more locations in the medium where the refractive index of the medium has been modified by the ultrasound; and
   wherein a beam of light directed into the medium is spatially patterned in the medium by the spatial pattern of refractive indices.

2. The method of claim 1 wherein the refractive index of the medium changes when one or more ultrasonic standing waves are induced in the medium by the one or more transducer elements, thereby causing an oscillation in the density of the medium.

3. The method of claim 2 wherein the transducer elements are arranged in a cylindrical pattern.

4. The method of claim 3 wherein the refractive index profile can be arranged in m azimuthal modes, wherein the m$^{th}$ azimuthal mode produces a refractive index profile exhibiting 2m nodes of pressure extrema.

5. The method of claim 4 wherein the nodes of pressure extrema are created by varying the phase of the ultrasound produced by the transducer array.

6. The method of claim 5 wherein the light beam is confined at locations of pressure extrema of the refractive index profile.

7. The method of claim 6:
   wherein the light beam is fragmented into multiple beams of light by the spatial pattern of refractive indices; and
   wherein the fragmented light beam may be coupled to the locations of the pressure extrema by applying stroboscopic illumination and inducing a phase shift between the light beam and a driving voltage signal of the transducer elements.

8. The method of claim 1 wherein the refractive index profile is created when the transducer elements are driven at different azimuthal modes.

9. The method of claim 8 wherein the azimuthal mode is created by applying a voltage vector to the transducer array, the voltage vector specifying the sign of the voltage to be applied to each transducer element.

10. The method of claim 9 wherein each transducer element has a positive and negative electrode and further wherein the transducer elements are driven by applying a driving voltage polarization azimuthally using a differential driving technique in which a positive pole of an amplifier output is connected to positive electrodes of the transducer elements and a negative pole of the amplifier is connected to negative electrodes of the transducer elements.

11. The method of claim 9 wherein the refractive index profile can be rotated by rotating the voltage vector among the transducer elements.

12. The method of claim 1 wherein the refractive index profile is created by the interference between ultrasonic waves produced by the one or more transducer elements.

13. The method of claim 1 wherein the refractive index profile can be condensed or expanded by changing the frequency of ultrasound produced by each transducer element of the transducer array.

14. The method of claim 1 wherein the light beam is patterned within the medium based on refraction due to the spatial pattern of refractive indices.

15. The method of claim 1 wherein the light beam is fragmented into multiple beams of light by the spatial pattern of refractive indices.

16. The method of claim 15 further comprising:
modulating the ultrasound produced by each transducer element to pattern the fragmented light beams such that the fragmented light beams are focused on multiple nodes with the medium.

17. An apparatus for creating a light wave guide in a medium comprising:
a multi-segment transducer directing ultrasound produced by a transducer array comprising one or more transducer elements into the medium to create a refractive index profile comprising a spatial pattern of refractive indices in the medium; and
an amplifier for applying a voltage to each transducer element;
wherein the spatial pattern of refractive indices comprises two or more locations in the medium where the refractive index of the medium has been modified by the ultrasound; and
wherein a beam of light directed into the medium is spatially patterned in the medium by the spatial pattern of refractive indices; and
wherein a beam of light directed into the medium is spatially patterned in the medium by the spatial pattern of refractive indices.

18. The apparatus of claim 17 wherein:
the refractive index profile is created when the transducer elements are driven at different azimuthal modes; and
the azimuthal mode is created by applying a voltage vector to the transducer array, the voltage vector specifying the sign of the voltage to be applied to each transducer element.

19. The apparatus of claim 18 wherein the refractive index profile can be rotated by rotating the voltage vector among the transducer elements.

20. The apparatus of claim 17 wherein the refractive index profile can be condensed or expanded by changing frequency of ultrasound produced by the transducer elements.

21. The apparatus of claim 17 wherein the beam of light is spatially patterned so as to be confined at locations of pressure extrema of the refractive index profile.

* * * * *

UNITED STATES PATENT AND TRADEMARK OFFICE
CERTIFICATE OF CORRECTION

PATENT NO. : 10,857,394 B2
APPLICATION NO. : 16/522230
DATED : December 8, 2020
INVENTOR(S) : Maysamreza Chamanzar, Yasin Karimi and Matteo Giuseppe Scopelliti It is certified that error appears in the above-identified patent and that said Letters Patent is hereby corrected as shown below:

In the Claims

Column 12, Claim 17, Lines 14-19; Please replace "wherein a beam of light directed into the medium is spatially patterned in the medium by the spatial pattern of refractive indices; and
    wherein a beam of light directed into the medium is spatially patterned in the medium by the spatial pattern of refractive indices." with --wherein a beam of light directed into the medium is spatially patterned in the medium by the spatial pattern of refractive indices.--

Signed and Sealed this
Twentieth Day of April, 2021

Drew Hirshfeld
*Performing the Functions and Duties of the
Under Secretary of Commerce for Intellectual Property and
Director of the United States Patent and Trademark Office*